US011332576B2

(12) United States Patent
Malet et al.

(10) Patent No.: US 11,332,576 B2
(45) Date of Patent: May 17, 2022

(54) BLOCK COPOLYMER DERIVED FROM RENEWABLE MATERIALS AND METHOD FOR MAKING SUCH A BLOCK COPOLYMER

(75) Inventors: Frederic Malet, Rouen (FR);
Guillaume Le, Colombelles (FR);
Julien Jouanneau, Corneville sur Risle (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 13/639,662

(22) PCT Filed: Apr. 5, 2011

(86) PCT No.: PCT/FR2011/050754
§ 371 (c)(1),
(2), (4) Date: Oct. 5, 2012

(87) PCT Pub. No.: WO2011/124833
PCT Pub. Date: Oct. 13, 2011

(65) Prior Publication Data
US 2013/0022771 A1 Jan. 24, 2013

(30) Foreign Application Priority Data
Apr. 7, 2010 (FR) ........................................ 1052617

(51) Int. Cl.
| | | |
|---|---|---|
| *C08G 65/26* | (2006.01) | |
| *C08G 69/40* | (2006.01) | |
| *C08G 63/672* | (2006.01) | |
| *C12P 7/10* | (2006.01) | |
| *C12P 5/02* | (2006.01) | |
| *C08L 71/02* | (2006.01) | |
| *C07D 301/02* | (2006.01) | |
| *C08G 18/48* | (2006.01) | |

(52) U.S. Cl.
CPC ........... *C08G 69/40* (2013.01); *C07D 301/02* (2013.01); *C08G 18/48* (2013.01); *C08G 63/672* (2013.01); *C08L 71/02* (2013.01); *C12P 5/026* (2013.01); *C12P 7/10* (2013.01); *Y02E 50/10* (2013.01); *Y10T 428/139* (2015.01); *Y10T 428/249921* (2015.04); *Y10T 442/30* (2015.04); *Y10T 442/60* (2015.04)

(58) Field of Classification Search
CPC .......... C08L 71/00; C08L 71/02; C08L 77/12; C08L 77/02; C08G 69/40; C08G 18/48; C08G 18/10; C08G 18/341; C08G 18/4825; C09D 301/02; Y02E 50/16; C08J 2377/00; C08J 2377/02; C09G 69/44; Y10T 428/139; Y10T 428/1393; Y10T 428/1397
USPC ........................................ 525/408, 411, 419
See application file for complete search history.

(56) References Cited

U.S. PATENT DOCUMENTS

| | | | | |
|---|---|---|---|---|
| 6,004,784 A | * | 12/1999 | Mobley et al. | ................ 435/134 |
| 6,784,257 B2 | | 8/2004 | Hilgers et al. | |
| 7,799,838 B2 | | 9/2010 | Vollenberg et al. | |
| 2003/0139539 A1 | | 7/2003 | Hilgers et al. | |
| 2007/0066725 A1 | * | 3/2007 | Malet | ..................... A43B 13/04 |
| | | | | 524/99 |
| 2007/0106034 A1 | * | 5/2007 | Linemann | .............. C08G 69/40 |
| | | | | 525/419 |
| 2008/0023887 A1 | | 1/2008 | Vollenberg et al. | |
| 2008/0312485 A1 | | 12/2008 | Takai et al. | |
| 2009/0017246 A1 | * | 1/2009 | Malet | ..................... C08G 69/40 |
| | | | | 428/36.9 |
| 2009/0050535 A1 | | 2/2009 | Evans | |
| 2010/0227938 A1 | | 9/2010 | Bauer et al. | |
| 2010/0234539 A1 | * | 9/2010 | Malet | ............................ 525/436 |
| 2011/0028609 A1 | * | 2/2011 | Lawson | ......................... 524/47 |

FOREIGN PATENT DOCUMENTS

| | | | | |
|---|---|---|---|---|
| CN | 1273256 A | 11/2000 | | |
| CN | 101304963 A | 11/2008 | | |
| EP | 1046675 A1 | 10/2000 | | |
| EP | 1953129 A1 | 8/2008 | | |
| EP | 2252647 A1 | * | 11/2010 | ............. C08G 69/40 |
| JP | 2009-91694 A | 4/2009 | | |
| WO | 2007/085548 A1 | 8/2007 | | |
| WO | WO 2008071894 A2 | * | 6/2008 | |
| WO | 2009/112369 A1 | 9/2009 | | |
| WO | WO 2009112369 A1 | * | 9/2009 | ............. C08G 69/40 |
| WO | WO-2009112369 A1 | * | 9/2009 | ............. C08G 69/40 |

OTHER PUBLICATIONS

Bruscino M, Biorefineries: Fact or Fiction, Aug. 2009, Hydrocarbon Processing, vol. 88, issue 8, pp. 65-70.*
Croda Polymers and Coatings, high performance Oleochemicals, Mar. 30, 2009, p. 3.*
University of Wisconsin, Madison (Nov. 26, 2001). Corn Yields Another Useful Product: Polypropylene Glycol. ScienceDaily. Retrieved Apr. 5, 2016 from www.sciencedaily.com/releases/2001/11/011120051947.htm.*
Sharma, Dinesh; A Handbook of Polymer Chemistry, Int. Scientific Publishing Academy, New Dehli, 2005, p. 152.*
Van Haveren et al., Bulk chemicals from biomass, biofuels, bioproducts, and biorefining. Wiley Interscience, Dec. 19, 2007, pp. 49, 50, and 55. (Year: 2007).*
Plotnik et al., Green propylene: process technology (including bioethanol, biobutanol, biodiesel, biomass, and vegetable oil routes) production, costs, and regional supply/demand forecasts (PERP07/08S11), Nexant, San Francisco, 2009 (Year: 2009).*

(Continued)

*Primary Examiner* — Lee E Sanderson
(74) *Attorney, Agent, or Firm* — Buchanan Ingersoll & Rooney P.C.

(57) ABSTRACT

The invention relates to a block copolymer derived from at least one ethylene oxide and/or propylene oxide monomer containing $^{14}C$.
The present invention also relates to a method for preparing such a block copolymer.

30 Claims, No Drawings

(56) References Cited

OTHER PUBLICATIONS

Morschbacker, A., "Bio-Ethanol Based Ethylene," Journal of Macromolecular Science: Part C—Polymer Reviews, Apr. 2, 2009, vol. 49, pp. 79-84, Taylor & Francis Inc. Philadelphia, PA, US; Cited in International Search Report, dated Jul. 20, 2011, issued in corresponding PCT/FR2011/050754.
International Search Report, dated Jul. 20, 2011, issued in corresponding PCT/FR2011/050754.
Office Action (Text of the Notice of Reexamination) dated Aug. 5, 2021, by the National Intellectual Property Administration, P. R. China in corresponding Chinese Patent Application No. 201710218130. 6, English Translation only. (11 pages).

* cited by examiner

BLOCK COPOLYMER DERIVED FROM RENEWABLE MATERIALS AND METHOD FOR MAKING SUCH A BLOCK COPOLYMER

FIELD OF THE INVENTION

The present invention relates to thermoplastic elastomers (TPE), and notably engineering polymers of high added value used in various sectors, such as electronics, automobiles or sports. The present invention relates more particularly to a thermoplastic elastomer derived from renewable raw materials. The invention also relates to a method of making said thermoplastic elastomer derived from renewable materials.

In conventional thermoplastic elastomers, we essentially find ingredients of petroleum origin or of synthetic origin. Their methods of production are sometimes regarded as causing environmental pollution. In fact, the raw materials used for synthesis of these ingredients are obtained by steam cracking or catalytic cracking of petroleum fractions. Use of these materials contributes to the increase in the greenhouse effect. With decreasing world petroleum reserves, the sources of these raw materials are gradually being exhausted.

Raw materials derived from biomass are from a renewable source and have a reduced impact on the environment. They do not require all the energy-consuming refining stages of petroleum products. Production of $CO_2$ is reduced, so that they contribute less to global warming.

It therefore appears necessary to have methods of synthesis that are not dependent on raw materials of fossil origin, but instead use raw materials of renewable origin.

Nowadays, manufacturers who use TPEs are increasingly adopting an eco-design approach and are searching for plastics of high added value of vegetable origin.

Moreover, in competitive markets such as sports or the car industry, manufacturers must meet consumers' demands for polymer materials combining technical and environmental performance. Now, said performance depends both on the raw materials and on the processes used.

The present invention therefore has the aim of providing TPEs that meet these requirements, both in terms of mechanical properties, chemical resistance or resistance to aging, and in terms of ecological ethics.

PRIOR ART

Thermoplastic elastomer (TPE) means a block copolymer comprising alternating blocks or segments that are called hard or rigid (rather with thermoplastic behavior) and blocks or segments that are pliable or flexible (rather with elastomeric behavior).

A block is said to be "pliable" if it has a low glass transition temperature (Tg). Low glass transition temperature means a glass transition temperature Tg of less than 15° C., preferably less than 0° C., advantageously less than −15° C., even more advantageously less than −30° C., and optionally less than −50° C.

The flexible blocks are generally based on polyethers (PE) selected from poly(ethylene glycol) (PEG), poly(1,2-propylene glycol) (PPG), poly(1,3-propylene glycol) (PO3G), poly(tetramethylene glycol) (PTMG), and copolymers or blends thereof. The rigid blocks are generally based on polyamide, polyurethane, polyester or a mixture of these polymers.

As examples of copolymers with rigid blocks and with flexible blocks, we may mention respectively (a) copolymers with polyester blocks and polyether blocks (also called COPE or copolyetheresters), (b) copolymers with polyurethane blocks and polyether blocks (also called TPU, abbreviation of thermoplastic polyurethanes) and (c) copolymers with polyamide blocks and polyether blocks (also called PEBA according to IUPAC).

In the field of thermoplastic elastomers such as TPU or COPE, products manufactured partially from raw materials of renewable origin have recently been marketed. As an example, the TPUs marketed under the brand name Pearlthane® ECO-D12T95 by Merquinsa claim a proportion of renewable carbon of 38% according to ASTM-D6866. We may also mention the COPE range marketed under the brand name Hytrel® RS by Dupont. This COPE comprises a PO3G derived from renewable resources that replaces petrochemical polyols.

As for the PEBAs, they are mainly obtained from raw materials of fossil origin, as only these make it possible to achieve the cost/performance compromise required for certain applications.

In fact, the PEBAs or Polyether-Block-Amides, such as those marketed by the company Arkema under the name Pebax®, are plasticizer-free thermoplastic elastomers which belong to the class of engineering polymers. They can be processed easily by injection molding and extrusion of shapes or films. They can also be used in the form of filaments, threads and fibers for woven fabrics and nonwovens. They are used in applications of high added value and in particular:
- high-level sport, notably as elements of soles of footwear for sprinting, football, rugby, tennis, basket-ball, running, Alpine or Nordic skiing, as well as in golf balls, and in many other sports articles;
- in industry, notably as conveyor belts, as breathable rainwear or as antistatic additive;
- in the medical field, notably as catheters, angioplasty balloons, peristaltic band;
- automobile, notably as synthetic leather, skin panels, instrument panels, airbag components, etc.

They make it possible to combine, in a single polymer, unequalled mechanical properties and very good resistance to thermal or UV aging, as well as low density. They thus make it possible to produce lightweight components. In particular, at equivalent hardness, they dissipate less energy than other materials, which endows them with very good resistance to dynamic stresses in bending or tension, and they have exceptional properties of elastic springback.

The PEBAs comprising polyamide blocks and PEG blocks also have well-known permanent antistatic properties and provide the films with breathable waterproof properties and leakproof properties, as described in patents EP 1046675 and EP 0737709.

Since 2007, the "Pebax® Rnew" range marketed by Arkema is the only one to offer a range of engineering-grade thermoplastic elastomers in which the proportion of carbon of renewable origin varies from about 20% to 95%, depending on the content of polyamide of renewable origin in the thermoplastic elastomer. In fact the classical PEBA is a thermoplastic elastomer obtained from polyamide 12 (or from polyamide 6) for the rigid block and from polyether for the flexible block, these two blocks being made from materials of fossil origin.

For the rigid block, a first move towards developing renewable raw materials consisted of selecting a polyamide made from raw materials of vegetable origin, such as amino-11-undecanoic acid. In fact, amino-11-undecanoic acid is obtained from the processing of castor oil, extracted from the plant of the same name (*Ricinus communis*, the castor-oil plant), from the seeds of the castor-oil plant. Replacement of PA 12 with PA 11, obtained by polycondensation of amino-11-undecanoic acid, in the manufacture of PEBA provides, in addition to a reduced environmental impact, a material for which certain properties are superior to those of the material of fossil origin. In particular, the PEBAs manufactured on the basis of PA 11 no longer have a plasticity threshold when submitted to stress, giving an improvement not only in low-temperature impact strength, but also in bending fatigue strength. The heat resistance is also improved, along with increased stiffness at low temperature.

However, for the polyether flexible block there is at present no renewable alternative other than the PO3G polyether blocks recently put on the market by Dupont under the brand name Cerenol®, or else the flexible polyesters, based on dimerized fatty acid, marketed by Uniqema under the brand name Priplast®. However, use of PO3G polyether blocks alone or Priplast® polyester blocks alone for making PEBAs does not allow the same performance to be achieved as with PEG blocks, in terms of density, take-up of water and/or mechanical properties, antistatic properties, breathable waterproof properties and leakproof properties. Moreover, the use of these PO3G or polyester blocks does not make it possible to readily modulate both the mechanical and antistatic properties of the block copolymer. Furthermore, the use of these PO3G blocks does not allow the same performances to be achieved as with PPG blocks, in terms of low take-up of moisture, and in particular in terms of stability of the mechanical properties with respect to ambient moisture.

The present invention therefore has the aim of devising a novel TPE that is of renewable origin and offers high performance. The present invention notably has the aim of supplying a TPE of renewable origin, but with performance at least equivalent to those of the conventional TPEs of fossil origin.

The present invention also has the aim of supplying a method of manufacture of said TPE that is simple, easy to apply, rapid (with the fewest possible stages), and that does not involve chemical or technological manipulations that are arduous, energy-consuming or polluting, so as to have the smallest possible environmental impact. In particular, the present invention has the aim of providing such a method that is easy to modulate, i.e. that is easy to adapt according to the desired antistatic, antiperspirant and mechanical properties.

Armed with its expertise in the manufacture of high-performance bioresourced polymers, the applicant was now able to demonstrate that it is possible to produce a TPE:

in which the polyether flexible blocks are of renewable origin, owing to the use of ethylene oxide and/or propylene oxide containing $^{14}C$, notably owing to the use of PEG and/or PPG blocks made from biomass, and
whose performance is at least identical to that of the corresponding TPEs whose polyether blocks are of fossil origin.

SUMMARY OF THE INVENTION

The invention relates to a block copolymer derived from at least one ethylene oxide and/or propylene oxide monomer containing $^{14}C$. Advantageously, said copolymer comprises at least one polyether block derived at least partially from ethylene oxide and/or propylene oxide containing $^{14}C$.

Advantageously, the block copolymer according to the invention comprises:
from 1 to 99% of at least one polyether flexible block derived at least partially from ethylene oxide and/or propylene oxide containing $^{14}C$, and
from 1 to 99% of at least one rigid block selected from: polyamide blocks, polyurethane blocks, polyester blocks, and mixtures thereof.

Advantageously, said at least one polyether flexible block comprises at least one polyethylene glycol (PEG) and/or polypropylene glycol (PPG) derived at least partially from renewable materials. Advantageously, the proportion by mass of said at least one flexible block represents from 5 to 95%, preferably from 5 to 85%, and the proportion by mass of said at least one rigid block represents from 5 to 95%, preferably from 15 to 95% of the total mass of the copolymer.

Advantageously, said at least one rigid block is derived at least partially from renewable raw materials.

Advantageously, said at least one polyether block and/or said at least one rigid block is/are derived totally from renewable materials.

Advantageously, the copolymer according to the invention has a biocarbon content of at least 1%, which corresponds to a $^{14}C/^{12}C$ isotope ratio of at least $1.2 \times 10^{-14}$. Advantageously, the copolymer according to the invention has a biocarbon content above 5%, preferably above 10%, preferably above 25%, preferably above 50%, preferably above 75%, preferably above 90%, preferably above 95%, preferably above 98%, preferably above 99%, advantageously roughly equal to 100%, which corresponds to a $^{14}C/^{12}C$ isotope ratio of $1.2 \times 10^{-12}$.

Advantageously, the copolymer according to the invention comprises at least one polyamide block. Advantageously, said polyamide comprises a copolyamide. Advantageously, the copolymer according to the invention comprises at least one polyamide block comprising at least one of the following molecules: amino-11-undecanoic acid, n-heptylamino-11-undecanoic acid, succinic acid, azelaic acid, sebacic acid, dodecanedioic acid, myristic acid, tetradecanedioic acid, hexadecanedioic acid, octadecanedioic acid, butanediamine, pentanediamine, decamethylenediamine, fatty diacid(s), fatty acid dimer(s) and mixtures thereof. Advantageously, said at least one polyamide block comprises at least one monomer selected from the following polyamide monomers: 11, 5.4, 5.9, 5.10, 5.12, 5.13, 5.14, 5.16, 5.18, 5.36, 6.4, 6.9, 6.10, 6.12, 6.13, 6.14, 6.16, 6.18, 6.36, 10.4, 10.9, 10.10, 10.12, 10.13, 10.14, 10.16, 10.18, 10.36, 10.T, 12.4, 12.9, 12.10, 12.12, 12.13, 12.14, 12.16, 12.18, 12.36, 12.T and blends or copolymers thereof. Advantageously, the block copolymer according to the invention is a copolymer with polyether blocks and polyamide blocks (abbreviated: PEBA).

Advantageously, said PEBA is based on PA11-PEG, PA10.10-PEG, PA10.12-PEG, PA10.14-PEG, PA6.10-PEG, PA6.12-PEG, PA6.18-PEG, PA11-PPG, PA10.10-PPG, PA10.12-PPG, PA10.14-PPG, PA6.10-PPG, PA6.12-PPG, PA6.18-PPG, PA11-PEG/PPG, PA10.10-PEG/PPG, PA10.12-PEG/PPG, PA10.14-PEG/PPG, PA6.10-PEG/PPG, PA6.12-PEG/PPG, and/or PA6.18-PEG/PPG, preferably based on PA11-PEG, PA11-PPG or PA11-PEG/PPG.

Advantageously, the copolymer according to the invention comprises at least one polyester block. Advantageously, said polyester comprises a copolymer. Advantageously, said at least one polyester block comprises at least one of the following molecules: ethylene glycol, 1,3-propanediol, 1,4-butanediol, 1,10-decanediol, dimerized fatty acid reduced to obtain the corresponding diol, 2,5-furandicarboxylic acid, succinic acid, azelaic acid, sebacic acid, dodecanedioic acid, myristic acid, tetradecanedioic acid, hexadecanedioic acid, octadecanedioic acid, and/or dimerized fatty acids.

Advantageously, said copolymer according to the invention is a polyetherester.

Advantageously, the copolymer according to the invention comprises at least one polyurethane block. Advantageously, said polyurethane comprises a copolymer, i.e. a copolyurethane. Advantageously, said at least one polyurethane block is made from at least one polyol of renewable origin, selected from the following polyols: polyols derived from starch; erythritol; sorbitol; maltitol; mannitol; polyols derived from sugars, sucrose; isomalt; xylitol; polyols derived from maize, soya, cotton, colza, sunflower or peanut; glycerol; propylene glycol; ethylene glycol; reaction coproducts from biodiesel production; polyethylene glycol (PEG), poly(1,2-propylene glycol) (PPG), poly(1,3-propylene glycol) (PO3G), polytetramethylene glycol (PTMG). Advantageously, said copolymer according to the invention is a polyetherurethane.

Advantageously, said at least one polyether block additionally comprises polyethers other than PEG and/or PPG, such as PO3G, PTMG, poly(3-methyltetrahydrofuran) of renewable origin or of fossil origin and/or PEG or PPG of fossil origin.

Advantageously, the copolymer according to the invention is a segmented block copolymer comprising three different types of blocks (called triblock hereinafter), said triblock being selected from copolyetheresteramides, copolyetheramideurethanes, copolyetheresterurethanes, in which:

the percentage by mass of polyether flexible block is above 20%;
the percentage by mass of polyamide rigid block is above 10%;

of the total mass of triblock.

The present invention also relates to a method for preparing block copolymer as defined previously, comprising the stage of supplying polyether derived at least partially from ethylene oxide and/or propylene oxide containing $^{14}C$ and conversion by synthesis to block copolymer. Advantageously, said polyether comprises polyethylene glycol and/or polypropylene glycol having a biocarbon content of at least 1%.

Advantageously, the supply stage comprises a stage of production of polyether from ethylene oxide and/or propylene oxide having a biocarbon content of at least 1%. Advantageously, the supply stage comprises a stage of production of said ethylene oxide and/or propylene oxide respectively from ethylene and/or propylene. Advantageously, the supply stage comprises a stage of production of said ethylene and/or propylene from plant biomass. Advantageously, said ethylene and/or propylene is produced by dehydration of bioethanol and/or isopropanol.

The present invention also relates to the use of the block copolymer as defined previously, in the automobile industry, textiles, woven fabrics, nonwovens, clothing, shoes, sports articles, leisure articles, electronics, computer equipment, health equipment, industrial additives, packaging and/or household products.

Advantageously, the block copolymer according to the invention is used in instrument panels, airbags, soles of sports shoes, golf balls, tubes for medical use, catheters, angioplasty balloons, peristaltic bands, conveyor belts, breathable waterproof rainwear, antistatic additives, skin panels, synthetic leather, thermoplastic films and/or packaging films.

Advantageously, the block copolymer of the invention is used alone or mixed, said copolymer representing by mass from 5 to 100%, preferably from 5 to 70%, preferably from 5 to 30%.

DETAILED DESCRIPTION OF THE INVENTION

The invention uses products of natural origin as starting products for making thermoplastic elastomers.

The carbon of a biomaterial comes from the photosynthesis of plants and therefore from atmospheric $CO_2$. The degradation (degradation will also be used with the meaning of combustion/incineration at the end of life) of these materials to $CO_2$ therefore does not contribute to global warming since there is no increase in carbon discharged into the atmosphere. The $CO_2$ balance of biomaterials is therefore much better and contributes to a reduction of the carbon footprint of the products obtained (only the energy for manufacture has to be taken into account). In contrast, when a material of fossil origin also degrades to $CO_2$ it will contribute to the increase in the proportion of $CO_2$ and therefore to global warming. The compounds according to the invention will therefore have a better carbon footprint than that of compounds obtained from a fossil source. The invention therefore also improves the ecological balance during manufacture of TPEs.

The term "biocarbon" indicates that the carbon is of renewable origin, or of natural origin and is from a biomaterial, as indicated below. The biocarbon content, the $^{14}C$ content and the content of biomaterial are expressions denoting the same value.

A material of renewable origin, or biomaterial, is an organic material in which the carbon comes from $CO_2$ fixed recently (on the human scale) by photosynthesis from the atmosphere. On land, this $CO_2$ is captured or fixed by plants. In the sea, the $CO_2$ is captured or fixed by bacteria or by plankton carrying out photosynthesis. A biomaterial (100% carbon of natural origin) has a $^{14}C/^{12}C$ isotope ratio greater than $10^{-12}$, typically of the order of $1.2 \times 10^{-12}$, whereas a fossil material has a ratio of zero. In fact, the $^{14}C$ isotope forms in the atmosphere and is then integrated by photosynthesis, on a time scale of some decades at most. The half-life of $^{14}C$ is 5730 years. Therefore materials derived from photosynthesis, namely plants in general, necessarily have a maximum content of isotope $^{14}C$.

The presence of $^{14}C$, the content of biomaterial, the content of biocarbon or the content of organic carbon of renewable origin of a material is determined on the basis of standards ASTM D 6866 (ASTM D 6866-06) and ASTM D 7026 (ASTM D 7026-04). Standard ASTM D 6866 relates to "Determining the Biobased Content of Natural Range Materials Using Radiocarbon and Isotope Ratio Mass Spectrometry Analysis", whereas standard ASTM D 7026 relates to "Sampling and Reporting of Results for Determination of Biobased Content of Materials via Carbon Isotope Analysis". The second standard refers in its first paragraph to the first standard. The first standard describes a test for measuring the $^{14}C/^{12}C$ ratio of a sample and compares it with the $^{14}C/^{12}C$ ratio of a reference sample of 100% renewable origin, to give a relative percentage of C of renewable origin in the sample. The standard is based on the same concepts as $^{14}C$ dating, but without applying dating equations. The ratio thus calculated is designated as "pMC" (percent Modern Carbon). If the material to be analyzed is a mixture of biomaterial and fossil material (without radioactive isotope), then the value of pMC obtained is directly correlated with the amount of biomaterial present in the sample. The reference value used for dating with $^{14}C$ is a value dating from the 1950s. This year was chosen because there were nuclear tests in the atmosphere, which introduced large amounts of isotopes into the atmosphere after this date. The reference 1950 corresponds to a pMC value of 100. Taking into account the thermonuclear tests, the present value to be adopted is about 107.5 (which corresponds to a correction factor of 0.93). The radioactive carbon signature of a plant today is therefore 107.5. A signature of 54 pMC and one of 99 pMC therefore correspond to an amount of biomaterial in the sample of 50% and 93%, respectively.

The standard ASTM D 6866 proposes three methods of measuring the content of isotope $^{14}C$:

LSC (Liquid Scintillation Counting) liquid scintillation spectrometry. This technique consists of counting Beta particles resulting from the disintegration of $^{14}C$. The Beta radiation from a sample of known mass (known number of C atoms) is measured over a certain time. This "radioactivity" is proportional to the number of $^{14}C$ atoms, which can thus be determined. The $^{14}C$ present in the sample emits β rays, which on contact with the scintillation fluid (scintillator) give rise to photons. These photons have different energies (between 0 and 156 keV) and form what is called a $^{14}C$ spectrum. According to two variants of this method, the analysis relates either to the $CO_2$ previously produced by the carbon-containing sample in a suitable absorbent solution, or to benzene after prior conversion of the carbon-containing sample to benzene. Standard ASTM D 6866 therefore gives two methods A and C, based on this LSC method.

AMS/IRMS (Accelerated Mass Spectrometry coupled with Isotope Radio Mass Spectrometry). This technique is based on mass spectrometry. The sample is reduced to graphite or to gaseous $CO_2$, analyzed in a mass spectrometer. This technique uses an accelerator and a mass spectrometer to separate the $^{14}C$ from the $^{12}C$ ions and thus determine the ratio of the two isotopes.

The compounds according to the invention come at least partly from biomaterial and therefore have a content of biomaterial of at least 1%, which corresponds to a content of $^{14}C$ of at least $1.2\times10^{-14}$. This content is advantageously higher, notably up to 100%, which corresponds to a content of $^{14}C$ of $1.2\times10^{-12}$. The compounds according to the invention can therefore comprise 100% of biocarbon or in contrast result from a mixture with a fossil origin.

The compounds according to the invention are, as mentioned above, thermoplastic elastomers (TPE) derived at least partially from raw materials of renewable origin.

More precisely, the present invention relates to thermoplastic elastomers (TPE), block copolymers, comprising at least one polyether block derived from at least one ethylene oxide and/or propylene oxide monomer containing $^{14}C$.

As polyethers that can be made from ethylene oxide containing $^{14}C$, we may mention poly(ethylene oxide), also called polyoxyethylene glycol or more commonly called poly(ethylene glycol) or polyethylene glycol (abbreviated to PEG). As polyethers that can be made from propylene oxide containing $^{14}C$, we may mention poly(propylene oxide), also called polyoxypropylene glycol or more commonly called poly(1,2-propylene glycol) or polypropylene glycol (abbreviated to PPG).

The polyether blocks of the TPEs according to the invention are obtained at least partially from raw materials of renewable origin and comprising at least one unit —O—$(CH_2)_2$— and/or at least one unit —O—$CHCH_3$—$(CH_2)$—, in which the carbons are biocarbons.

Polyether blocks (hereinafter abbreviated to PE) mean, in the sense of the invention, polyalkylene ether polyols, notably polyalkylene ether diols. Said at least one PE block of the copolymer of the invention comprises at least poly(ethylene glycol) (PEG) and/or polypropylene glycol (PPG) of at least partially renewable origin, but the PE block(s) of the copolymer of the invention can additionally comprise other PEs of renewable origin or of fossil origin, selected from poly(ethylene glycol) (PEG) and/or polypropylene glycol (PPG) of non-renewable origin, poly (1,2-propylene glycol) (PPG), polytetramethylene ether glycol (PTMG), polyhexamethylene glycol, poly(1,3-propylene glycol) (PO3G), poly(3-alkyl tetrahydrofuran) in particular poly(3-methyltetrahydrofuran (poly(3MeTHF)), and mixtures thereof. A PE block of the block or random "copolyether" type containing a chain of at least two types of PE mentioned above can also be envisaged.

The polyether blocks can also comprise blocks obtained by ethoxylation of bisphenols, for example bisphenol A. These last-mentioned products are described in patent EP 613 919. The polyether blocks can also comprise ethoxylated primary amines. Advantageously these blocks are also used. As examples of ethoxylated primary amines we may mention the products of formula:

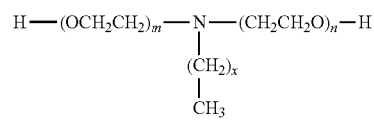

in which m and n are between 1 and 20 and x is between 8 and 18. These products are available commercially under the brand name NORAMOX® from the company CECA and under the brand name GENAMIN® from the company CLARIANT.

Thus, the chain ends of the PE blocks can be diOH, diNH2, diisocyanate or diacid depending on their method of synthesis. The PE blocks with NH2 chain ends can be obtained by cyanoacetylation of aliphatic dihydroxylated alpha-omega polyoxyalkylene sequences called polyether diols such as Jeffamines® D300, D400, D2000, ED-600, ED-900, ED2003, the Elastamines® RP-409, RP-2009, RT-1000, RE-600, RE-900, RE-2000, HT-1700, HE-180 from the company Huntsman. Said blocks are described in patents JP 2004346274, JP 2004352794 and EP1482011.

According to one embodiment, said at least one polyether, for example PEG, is derived from at least one ethylene oxide monomer containing $^{14}C$, which is synthesized from ethylene which is itself synthesized from ethanol (bioethanol) or from a mixture of alcohols comprising ethanol. These alcohols are derived from the fermentation of renewable raw materials, in particular vegetable raw materials selected from sugar cane and sugar beet, maple, date palm, sugar palm, sorghum, American agave, corn, wheat, barley, sorghum, soft wheat, rice, potato, cassava, sweet potato and algae.

According to a second embodiment, said at least one polyether, for example PPG, is derived from at least one propylene oxide monomer (PPG) containing $^{14}C$, which is synthesized from propylene which is itself synthesized from an alcohol or from a mixture of alcohols, said alcohol or mixture of alcohols comprising at least isopropanol and/or at least a mixture of ethanol and of 1-butanol. These alcohols are themselves derivatives of renewable raw materials and are derived from the fermentation of vegetable materials selected from sugar cane and sugar beet, maple, date palm, sugar palm, sorghum, American agave, corn, wheat, barley, sorghum, soft wheat, rice, potato, cassava, sweet potato, and materials comprising cellulose or hemicellulose, such as wood, straw or paper.

These two embodiments of the invention are alternatives or can be combined, such that the polyether block comprises both PEG and PPG containing $^{14}C$, according to standard ASTM D6866.

The thermoplastic elastomers (TPE) according to the invention can additionally contain other flexible blocks that are not polyether-based. We may notably mention blocks based on polyesters such as poly(caprolactone) or polyesters of the Priplast® type, based on polydimethylsiloxane or PDMS, based on aliphatic polycarbonate, based on polyolefin such as polybutadiene, polyisobutylene etc.

Moreover, the thermoplastic elastomers (TPE) according to the invention comprise at least one rigid block selected from polyamide blocks, polyurethane blocks, polyester blocks, and mixtures thereof in the form of block or random copolymers.

The rigid blocks can be derived from renewable materials and/or from materials of fossil origin.

Advantageously, said rigid blocks are also derived at least partially from renewable materials. According to a particularly advantageous embodiment of the present invention, the polyether blocks and/or the polyamide blocks and/or the polyurethane blocks and/or the polyester blocks are derived totally from renewable materials.

Thus, depending on the choice of components of the flexible and rigid blocks, the biocarbon content of the copolymer of the invention is at least 1%, which corresponds to a $^{14}C/^{12}C$ isotope ratio of at least $1.2\times10^{-14}$. The biocarbon content of the copolymer of the invention is preferably above 5%, preferably above 10%, preferably above 25%, preferably above 50%, preferably above 75%, preferably above 90%, preferably above 95%, preferably above 98%, preferably above 99%. It is advantageously roughly equal to 100%, which corresponds to a $^{14}C/^{12}C$ isotope ratio of at least $1.2\times10^{-12}$.

According to a preferred embodiment, the block copolymer of the present invention comprises at least one polyether flexible block derived at least partially from ethylene oxide and/or propylene oxide containing $^{14}C$, preferably at least one PEG and/or PPG obtained at least in part from raw materials of renewable origin, and polyamide blocks.

Polyamide means, in the sense of the invention, homopolyamides and copolyamides; i.e. products of condensation of lactams, amino acids or diacids with diamines and, as a general rule, any polymer formed by units joined together by amide groups.

Polyamide of totally renewable origin that can be included in the copolymer according to the invention means:
aliphatic polyamides obtained from lactams or from amino acids (for example PA 11 obtained by polycondensation of amino-11-undecanoic acid);
the products of condensation of a dicarboxylic acid with a diamine (for example PA 10.10, the condensation product of decanediamine with sebacic acid, or PA 10.12, the condensation product of decanediamine with dodecanedioic acid, or PA 10.36, the condensation product of decanediamine with a fatty acid dimer);
the copolyamides resulting from the polymerization of various monomers, such as those mentioned above, for example the following copolyamides: PA 11/10.10, PA 11/10.12, PA 10.10/10.12, PA 11/10.36, PA 10.12/10.36, PA 10.10/10.36, the amino-11-undecanoic/n-heptyl-11-aminoundecanoic copolyamide, etc. Copolyamides of renewable origin, which comprise at least two monomers, are more particularly described in French patent application No.: 07.53319.

The term "monomer" in the present description of copolyamides must be understood in the sense of "repeating unit". In fact, a particular case is when a repeating unit of PA is constituted of a combination of a diacid with a diamine. It is considered that it is the combination of a diamine and of a diacid, i.e. the diamine.diacid couple (in equimolar amount), that corresponds to the monomer. This is explained by the fact that individually, the diacid or the diamine is only one structural unit, which in itself is not sufficient to polymerize.

As examples of amino acids of renewable origin, we may mention: 11-aminoundecanoic acid produced for example from castor oil, 10-aminodecanoic acid produced for example from decylenic acid obtained by metathesis of oleic acid, 9-aminononanoic acid produced for example from oleic acid.

As examples of diacids of renewable origin, we may mention, according to the number x of carbons in the molecule (Cx):
C4: succinic acid from glucose for example;
C6: adipic acid from glucose for example;
C7: heptanedioic acid from castor oil;
C9: azelaic acid from oleic acid (ozonolysis) for example;
C10: sebacic acid from castor oil for example;
C11: undecanedioic acid from castor oil;
C12: dodecanedioic acid from biofermentation of dodecanoic acid=lauric acid (rich oil: cabbage palm oil and coconut oil) for example;
C13: brassylic acid from erucic acid (ozonolysis) which occurs in colza for example;
C14: tetradecanedioic acid by biofermentation of myristic acid (rich oil: cabbage palm oil and coconut oil) for example;
C16: hexadecanedioic acid by biofermentation of palmitic acid (mainly palm oil) for example;
C18: octadecanedioic acid obtained by biofermentation of stearic acid (a little in all vegetable oils but chiefly in animal fats) for example;
C20: eicosanedioic acid obtained by biofermentation of arachidic acid (mainly in colza oil) for example;
C22: docosanedioic acid obtained by metathesis of undecylenic acid (castor oil) for example;
C36: fatty acid dimer derived principally from oleic and linoleic acids.

As examples of diamines of renewable origin, we may mention, according to the number x of carbons in the molecule (Cx):
C4: butanediamine obtained by amination of succinic acid, by biofermentation;
C5: pentamethylene diamine (from lysine);
and so on for the diamines obtained by amination of the diacids of renewable origin already discussed.

"Polyamide of partially renewable origin", i.e. derived only partly from renewable materials (called "mixed" polyamide in this document) means:
the products of condensation of a dicarboxylic acid with a diamine, and in which only one of the two (the diacid or the diamine) is of renewable origin. This applies for example to PA 6.10, since in the monomer 6.10, only the sebacic acid is of renewable origin, whereas the hexamethylene diamine is obtained from petrochemistry.

the copolyamides resulting from the polymerization of various monomers (renewable, nonrenewable or mixed) such as those mentioned above. This applies for example to CoPA 6.6/10.10 in which the monomer "6.6" is of nonrenewable origin whereas the monomer "10.10" is of renewable origin. This also applies to PA 11/10.T for example, which comprises a monomer of renewable origin ("11") and a mixed monomer of partially renewable origin ("10.T") since only the decanediamine is of renewable origin, whereas the terephthalic acid (T) is not.

"Polyamide of fossil origin" means all the other polyamides on the Earth that are not included in the two categories mentioned above, i.e. that are not made from renewable organic raw materials.

Advantageously, the block copolymer of the present invention forms a polyether block amide, abbreviated to PEBA.

The PEBAs according to the invention therefore include any TPE comprising at least one polyether block, the latter being derived at least partially from ethylene oxide and/or propylene oxide containing $^{14}C$, such as PEG and/or PPG respectively derived at least partially from renewable materials, and at least one PA block (homopolyamide or copolyamide) derived from fossil materials or else derived totally or partially (in the case of mixed polyamides) from renewable raw materials.

The PEBAs result from the polycondensation of polyamide blocks with reactive ends with polyether blocks with reactive ends, such as, among others:

1) polyamide blocks with diamine chain ends with polyoxyalkylene blocks with dicarboxylic chain ends.

2) polyamide blocks with dicarboxylic chain ends with polyoxyalkylene blocks with diamine chain ends, obtained by cyanoethylation and hydrogenation of aliphatic dihydroxylated alpha-omega polyoxyalkylene blocks called polyetherdiols 3) polyamide blocks with dicarboxylic chain ends with polyetherdiols, the products obtained being, in this particular case, polyetheresteramides.

The polyamide blocks with dicarboxylic chain ends result, for example, from the condensation of precursors of polyamides in the presence of a chain-limiting dicarboxylic acid. The polyamide blocks with diamine chain ends are obtained for example from the condensation of precursors of polyamides in the presence of a chain-limiting diamine. The number-average molecular weight Mn of the polyamide blocks is in the range from 400 to 20 000 g/mol, preferably from 500 to 10 000 g/mol, and more preferably from 600 to 6000 g/mol.

The polymers with polyamide blocks and polyether blocks can also comprise randomly distributed units.

The polyamide blocks can comprise homopolyamides or copolyamides. Three types of polyamides can be present in the composition of these PA blocks.

According to a first type, the polyamide blocks are derived from the condensation of at least one dicarboxylic acid (aliphatic, cycloaliphatic or aromatic) in particular those having from 4 to 36 carbon atoms, preferably those having from 6 to 18 carbon atoms and from at least one diamine (aliphatic, cycloaliphatic or aromatic) selected in particular from those having from 2 to 20 carbon atoms, preferably those having from 6 to 15 carbon atoms. As examples of aliphatic diacids, we may mention butanedioic, adipic, suberic, azelaic, sebacic, dodecanedicarboxylic, myristic, tetradecanedicarboxylic, hexadecane-dicarboxylic, octadecanedicarboxylic acids and the dimerized fatty acids. As examples of cycloaliphatic diacids, we may mention 1,4-cyclohexyldicarboxylic acid. As examples of aromatic diacids, we may mention terephthalic acid (T) and isophthalic acid (I). As examples of aliphatic diamines, we may mention tetramethylenediamine, hexamethylenediamine, 1,10-decamethylenediamine, dodecamethylenediamine, trimethyl-hexamethylenediamine. As examples of cycloaliphatic diamines, we may mention the isomers of bis-(4-aminocyclohexyl)-methane (BACM or PACM), bis-(3-methyl-4-aminocyclohexyl)-methane (BMACM or MACM), and 2-2-bis-(3-methyl-4-aminocyclohexyl)-propane (BMACP), isophoronediamine (IPDA), 2,6-bis-(aminomethyl)-norbornane (BAMN) and piperazine (Pip).

Advantageously, the copolymer according to the invention comprises at least one PA block based on PA 4.4, PA 4.6, PA 4.9, PA 4.10, PA 4.12, PA 4.14, PA 4.16, PA 4.18, PA 4.36, PA 6.4, PA 6.6, PA 6.9, PA 6.10, PA 6.12, PA 6.13, PA 6.14, PA 6.16, PA 6.18, PA 6.36, PA 9.4, PA 9.6, PA 9.10, PA 9.12, PA 9.14, PA 9.18, PA 9.36, PA 10.4, PA 10.6, PA 10.9, PA 10.10, PA 10.12, PA 10.13, PA 10.14, PA 10.16, PA 10.18, PA 10.36, PA 10.T, PA BMACM.4, PA BMACM.6, PA BMACM.9, PA BMACM.10, PA BMACM.12, PA BMACM.14, PA BMACM.16, PA BMACM.18, PA BMACM.36, PA PACM.4, PA PACM.6, PA PACM.9, PA PACM.10, PA PACM.12, PA PACM.14, PA PACM.16, PA PACM.18, PA PACM.36, PA Pip.4, PA Pip.6, PA Pip.9, PA Pip.10, PA Pip.12, PA Pip.14, PA Pip.16, PA Pip.18 and/or PA Pip.36, and mixtures thereof.

According to a second type, polyamide blocks result from the condensation of one or more alpha-omega aminocarboxylic acids and/or one or more lactams having from 6 to 12 carbon atoms in the presence of a dicarboxylic acid having from 4 to 12 carbon atoms or of a diamine. As examples of lactams, we may mention caprolactam, enantholactam and lauryllactam. As examples of alpha-omega aminocarboxylic acid, we may mention the aminocaproic, amino-7-heptanoic, amino-11-undecanoic and amino-12-dodecanoic acids.

Advantageously, the polyamide blocks of the second type are of polyamide 11, of polyamide 12 or of polyamide 6.

According to a third type, the polyamide blocks result from the condensation of at least one monomer of the first type with at least one monomer of the second type. In other words, the polyamide blocks result from the condensation of at least one alpha-omega aminocarboxylic acid (or a lactam), with at least one diamine and a dicarboxylic acid.

In this case, the PA blocks are prepared by polycondensation:

of aliphatic, cycloaliphatic or aromatic diamine(s) having X carbon atoms;

of dicarboxylic acid(s) having Y carbon atoms; and of comonomer(s) {Z}, selected from lactams and alpha-omega aminocarboxylic acids having Z carbon atoms;

in the presence of a chain limiter selected from dicarboxylic acids or diamines or an excess of diacid or of diamine used as structural unit.

Advantageously, the chain limiter used is a dicarboxylic acid having Y carbon atoms, which is introduced in excess relative to stoichiometry of the diamine or diamines.

According to another embodiment, the polyamide blocks result from the condensation of at least two different alpha-omega aminocarboxylic acids or of at least two different lactams having from 6 to 12 carbon atoms or of a lactam and an aminocarboxylic acid that does not have the same number of carbon atoms optionally in the presence of a chain limiter.

As examples of polyamide blocks of the third type, we may mention those formed by the following polyamides (copolyamides):

PA 6/6.6 in which 6 denotes caprolactam and 6.6 denotes a monomer resulting from the condensation of hexamethylenediamine with adipic acid.

PA 6.6/Pip.10/12 in which 6.6 denotes a monomer resulting from the condensation of hexamethylenediamine with adipic acid. Pip.10 denotes a monomer resulting from the condensation of piperazine with sebacic acid. 12 denotes lauryllactam.

PA 6.6/6.10/11/12 in which 6.6 denotes a monomer resulting from the condensation of hexamethylenediamine with adipic acid. 6.10 denotes a monomer resulting from the condensation of hexamethylenediamine with sebacic acid. 11 denotes amino-11-undecanoic acid. 12 denotes lauryllactam.

As examples, we may also mention PA 10.10/11, PA 6.10/11, PA10.12/11, PA 10.10/11/12, PA 6.10/10.10/11, PA 6.10/6.12/11, PA 6.10/6.12/10.10.

The polyether blocks can represent 1 to 99 wt. %, and preferably 5 to 90 wt. % of the copolymer with polyamide and polyether blocks. The molar mass Mn of the polyether blocks is in the range from 100 to 6000 g/mol and preferably from 200 to 3000 g/mol, even more preferably from 250 to 2000 g/mol.

The preparation of the copolymers with polyamide block(s) and polyether block(s) according to the invention comprises any means for attaching the polyamide blocks (PA blocks) and polyether blocks (PE blocks) according to the present invention. In practice, essentially two processes are used: a two-stage process and a one-stage process, these two processes being described in application FR0856752. Advantageously, the PEBA copolymers comprise PA blocks comprising at least one of the following polyamides PA 11, PA 10.10, PA 10.12, PA 10.14, PA 10.18, PA 6.10, PA 6.12, PA 6.14, PA 6.18 as principal components (percentage by mass above 50% of the total mass of PA) and PE blocks comprising PEG and/or PPG of renewable origin as principal component (percentage by mass above 50% of the total mass of PE), and optionally PO3G of renewable origin as other components of the PE blocks of the PEBA of the invention. Particularly preferred block copolymers of the invention are PA11-PEG, PA10.10-PEG, PA10.12-PEG, PA10.14-PEG, PA6.10-PEG, PA6.12-PEG, PA6.18-PEG, PA11-PPG, PA10.10-PPG, PA10.12-PPG, PA10.14-PPG, PA6.10-PPG, PA6.12-PPG, PA6.18-PPG, PA11-PEG/PPG, PA10.10-PEG/PPG, PA10.12-PEG/PPG, PA10.14-PEG/PPG, PA6.10-PEG/PPG, PA6.12-PEG/PPG, and/or PA6.18-PEG/PPG.

In particular, PA11-PEG, PA11-PPG or PA11-PEG/PPG according to the invention, of totally renewable origin, are preferred.

According to a second embodiment, the block copolymer of the present invention comprises at least one polyether flexible block which comprises at least one PEG and/or PPG glycol obtained at least in part from raw materials of renewable origin, and at least one polyester block.

Polyester means, in the sense of the invention, the products of condensation of dicarboxylic acids with diols, and as a general rule, any polymer whose macromolecular backbone contains repeating units containing the ester chemical function.

The polyester blocks (abbreviated hereinafter as PES blocks) are usually made by polycondensation between a dicarboxylic acid and a diol. Suitable carboxylic acids comprise those mentioned above used to form the polyamide blocks. Suitable diols comprise linear aliphatic diols such as ethylene glycol, 1,3-propylene glycol, 1,4-butylene glycol, 1,6-hexylene glycol, branched diols such as neopentylglycol, 3-methylpentane glycol, 1,2-propylene glycol, and cyclic diols such as 1,4-bis(hydroxymethyl)cyclohexane and 1,4-cyclohexane-dimethanol.

Advantageously, the block copolymer of the present invention forms a copolyetherester (abbreviation COPE), i.e. a copolymer with polyester and polyether blocks.

The COPEs according to the invention therefore include any TPE comprising at least one polyether block (PE) derived at least partly from ethylene oxide and/or propylene oxide comprising $^{14}C$, preferably comprising polyethylene glycol (or PEG) and/or polypropylene glycol (or PPG) derived at least partially from renewable materials, and at least one polyester block PES (homopolymer or copolyester) derived from fossil materials or else derived totally or partially (in the case of mixed polyesters) from renewable raw materials.

The COPEs comprise polyether flexible blocks derived from polyetherdiols and polyester rigid blocks, which result from reaction of at least one dicarboxylic acid with at least one chain-extending short diol unit. The polyester blocks and polyether blocks are joined by ester bonds resulting from the reaction of the acid functions of the dicarboxylic acid with the OH functions of the polyetherdiol. The chain-extending short diol can be selected from the group comprising neopentylglycol, cyclohexanedimethanol and aliphatic glycols of formula $HO(CH_2)_nOH$, in which n is an integer from 2 to 10. The chain of polyethers and diacids forms the flexible blocks, whereas the chain of glycol or of butanediol with the diacids forms the rigid blocks of the copolyetherester.

Advantageously, the diacids are aromatic dicarboxylic acids having from 8 to 14 carbon atoms. Up to 50 mol. % of the aromatic dicarboxylic acid can be replaced with at least one other aromatic dicarboxylic acid having from 8 to 14 carbon atoms, and/or up to 20 mol. % can be replaced with an aliphatic dicarboxylic acid having from 2 to 14 carbon atoms. As examples of aromatic dicarboxylic acids, we may mention terephthalic acid, isophthalic acid, dibenzoic acid, naphthalene dicarboxylic acid, 4,4'-diphenylenedicarboxylic acid, bis(p-carboxyphenyl)methane acid, ethylene-bis-p-benzoic acid, 1,4-tetramethylene-bis(p-oxybenzoic) acid, ethylene-bis-(p-oxybenzoic) acid, 1,3-trimethylene-bis-(p-oxybenzoic) acid. As examples of glycols, we may mention ethylene glycol, 1,3-trimethylene glycol, 1,4-tetramethylene glycol, 1,6-hexamethylene glycol, 1,3-propylene glycol, 1,8-octamethylene glycol, 1,10-decamethylene glycol and 1,4-cyclohexylene dimethanol.

The copolymers with polyester and polyether blocks are copolymers having polyether units derived from polyetherdiols as defined previously, for example polyethylene glycol (PEG), polypropylene glycol (PPG), polytrimethylene glycol (PO3G) or polytetramethylene glycol (PTMG), dicarboxylic acid units such as terephthalic acid and glycol units (ethanediol) or 1,4-butanediol. Said copolyetheresters are described in patents EP402883 and EP405227. These polyetheresters can also contain plasticizers and other additives that are well known by a person skilled in the art.

According to a third embodiment, the block copolymer of the present invention comprises at least one polyether flexible block derived at least partially from ethylene oxide and/or propylene oxide containing $^{14}C$, preferably comprising at least one polyethylene glycol and/or one polypropylene glycol obtained at least in part from raw materials of renewable origin, and at least one polyurethane rigid block.

Polyurethane (abbreviation PU) means, in the sense of the invention, the products resulting from the reaction of at least one diisocyanate which can be selected from the aromatic diisocyanates (e.g. MDI, TDI) and/or the aliphatic diisocyanates (e.g. HDI or hexamethylenediisocyanate) with at least one short diol. This chain-extending short diol can be selected from the glycols mentioned above in the description of the copolyetheresters. The polyurethanes included in the composition of the copolymers according to the invention can comprise all types of polyols, and in particular those of renewable origin, such as polyols derived from starch (erythritol, sorbitol, maltitol, mannitol), polyols derived from sugars such as sucrose (isomalt, xylitol), polyols derived from maize, soya, cotton, colza, sunflower or peanut (glycerol, propylene glycol, ethylene glycol, coproduct of the reaction for production of biodiesel). As other examples of polyols that can be included in the composition of these polyurethanes, we may also mention polyethylene glycol (PEG), poly(1,2-propylene glycol) (PPG), poly(1,3-propylene glycol) (PO3G), polytetramethylene glycol (PTMG), whether they are of petrochemical origin or renewable origin. Advantageously, the PEG and/or PPG produced from renewable materials will be used.

Advantageously, the block copolymer of the present invention forms a thermoplastic polyurethane (abbreviation TPU), i.e. a copolymer with polyurethane and polyether blocks, also called polyetherurethane.

The TPUs according to the invention therefore include any TPE comprising polyether blocks, the latter being derived at least in part from ethylene oxide and/or propylene oxide comprising $^{14}$C, including for example PEG and/or PPG derived at least partially from renewable materials; and PU blocks (homopolymer or copolyurethane) derived from fossil materials or else obtained totally or partially (in the case of mixed polyurethanes) from renewable raw materials, and said PU blocks can also be obtained from ethylene oxide and/or propylene oxide comprising $^{14}$C, and comprise for example PEG and/or PPG derived at least partially from renewable materials.

The polyetherurethanes result from the condensation of polyether flexible blocks, which are polyetherdiols, and of polyurethane rigid blocks. The polyurethane blocks and polyether blocks are joined together by bonds resulting from the reaction of the isocyanate functions of the polyurethane with the —OH functions of the polyetherdiol.

If the block copolymers described above generally comprise at least one polyether flexible block and at least one rigid block, it is evident that the present invention in fact covers all the copolymers comprising two, three, four (or even more) different blocks selected from those described in the present description, if at least one of these blocks is derived from at least one ethylene oxide and/or propylene oxide monomer containing $^{14}$C.

Advantageously, the copolymer according to the invention is a segmented block copolymer comprising three different types of blocks (called "triblock" in the present description of the invention), which result from the condensation of several of the blocks described above. Said triblock is preferably selected from copolyetheresteramides, copolyetheramideurethanes, copolyetheresterurethanes, in which:
 the percentage by mass of polyether flexible block is above 20%;
 the percentage by mass of polyamide rigid block is above 10%;

of the total mass of triblock.

The block copolymer of the invention can also be used alone or as a blend, said copolymer representing by mass from 5 to 100%, preferably from 5 to 70%, preferably from 5 to 30%, of the total mass of the blend.

The copolymer according to the invention can have as additives: stabilizers, plasticizers, lubricants, natural or organic fillers, dyes, pigments, nacres, antimicrobial agents, fireproofing agents, antistatic agents, agents modifying the viscosity of the copolymer, and/or any other additive well known by a person skilled in the art in the field of thermoplastic polymers.

The present invention also relates to a method for preparing a copolymer as defined above. The method according to the invention comprises the stage of supplying polyether (PE) derived at least partially from ethylene oxide and/or propylene oxide comprising $^{14}$C, and conversion by synthesis to the block copolymer according to the invention. Said conversion by synthesis leads to a block copolymer that comprises at least one PEG and/or PPG block of at least partially renewable origin. Preferably, said PE comprises PEG and/or PPG having a biocarbon content of at least 1%.

In particular, the preparation of the copolymers with polyamide block(s) and polyether block(s) according to the invention comprises any means for attaching the polyamide blocks (PA blocks) and polyether blocks (PE blocks) according to the present invention. In practice, essentially two processes are used: a two-stage process and a one-stage process.

In the one-stage process, the polyamide precursors, the chain limiter and the polyether are mixed together.

Thus, polyamide blocks are also produced in the one-stage process. The simultaneous polycondensation of the polyether blocks and of the precursors of the polyamide blocks is preferably carried out at a temperature from 180 to 300° C. A polymer is then obtained having essentially polyether blocks, polyamide blocks of very variable length, but also the various reactants that have reacted randomly, which are distributed statistically (randomly) along the polymer chain.

Whether using a one-stage process or a two-stage process, it is advantageous to work in the presence of a catalyst. "Catalyst" means any product that can facilitate bonding of the polyamide blocks and of the polyether blocks by esterification or by amidation. The esterification catalyst is advantageously a derivative of a metal selected from the group comprising titanium, zirconium and hafnium or a strong acid such as phosphoric acid or boric acid. The catalysts described in the following patents can be used: U.S. Pat. Nos. 4,331,786, 4,115,475, 4,195,015, 4,839,441, 4,864, 014, 4,230,838 and 4,332,920, WO 04 037898, EP 1262527, EP 1270211, EP 1136512, EP 1046675, EP 1057870, EP 1155065, EP 506495 and EP 504058.

In the two-stage process, the polyamide blocks are produced first, then in a second stage the polyamide blocks and polyether blocks are attached. The polyetherdiol blocks according to the invention are either used as they are and copolycondensed with polyamide blocks with carboxylic ends, or they are aminated, being converted to polyether diamines and condensed with polyamide blocks with carboxylic ends. The general method of two-stage preparation of PEBA copolymers having ester bonds between the PA blocks and the PE blocks is known and is described, for example, in French patent FR 2 846 332. The general method of preparation of the PEBA copolymers of the invention having amide bonds between the PA blocks and the PE blocks is known and is described for example in European patent EP 1 482 011.

The reaction of formation of the PA block is usually carried out between 180 and 300° C., preferably from 200 to 290° C., the pressure in the reactor is set between 5 and 30 bars, and it is maintained for about 2 to 3 hours. The pressure is reduced slowly, exposing the reactor to atmospheric pressure, then the excess water is distilled, for example for an hour or two.

Once the polyamide with carboxylic acid ends has been prepared, the polyether and a catalyst are added. The polyether can be added in one go or gradually, similarly for the catalyst. According to an advantageous embodiment, first some or all of the polyether is added; reaction of the OH ends of the polyether and of the COOH ends of the polyamide begins with formation of ester bonds and elimination of water. As much of the water as possible is removed from the reaction mixture by distillation, then the catalyst is introduced for bonding the polyamide blocks and polyether blocks. This second stage is carried out with stirring, preferably under a vacuum of at most 100 mbar, preferably of at most 50 mbar, preferably of at most 20 mbar, preferably at most 10 mbar, at a temperature such that the reactants and the copolymers obtained are in the molten state. As an example, this temperature can be between 100 and 300° C. and is generally between 200 and 250° C. The reaction is monitored by measurement of the torque exerted by the molten polymer on the stirrer or by measurement of the electric power consumed by the stirrer. The end of the reaction is determined by the target value of the torque or power.

It will also be possible to add during the synthesis, at the moment judged to be the most suitable, one or more molecules used as antioxidant, for example Irganox® 1010 or Irganox® 245.

According to one embodiment of the method of the invention, the stage of supplying PE in the method of the invention further comprises a prior stage of production of PEG and/or PPG polyether respectively from ethylene oxide (EO) and/or propylene oxide (PO) having a biocarbon content of at least 1%. Any known method for the production of PEG and/or PPG respectively from ethylene oxide (EO) and/or propylene oxide (PO) can be used for the present invention. Volume A21, page 583, of "Ullmann's Encyclopedia of Industrial Chemistry" describes these methods.

By way of example, low-molecular-weight polyethylene glycol (molecular weight less than 20 000) is produced by reacting ethylene oxide with water, ethylene glycol or ethylene glycol oligomers. The reaction is catalyzed by acid or basic catalysts, such as metal oxides or alkali metal oxides. Ethylene glycol and oligomers thereof are preferable to water as starting reactants, since they make it possible to obtain a polymer with a narrow molecular weight distribution (low polydispersity). The polymer chain length depends on the ratio between the reactants.

$HOCH_2CH_2OH + n(CH_2CH_2O) \rightarrow HO(CH_2CH_2O)_{n+1}H$

According to the type of catalyst, the polymerization mechanism may be cationic or anionic. The anionic mechanism is preferred since it makes it possible to obtain a PEG of low polydispersity. The polymerization (polycondensation) of ethylene oxide is an exothermic process.

High-molecular-weight polyethylene oxide (greater than 20 000) is synthesized by suspension polymerization. During the polycondensation process, it is necessary to maintain the growing polymer chain in solution. This reaction is catalyzed by organometallic magnesium, aluminum or calcium compounds, for example. In order to prevent coagulation of the polymer chains out of the solution, chelating additives such as dimethylglyoxime are used.

Alkali metal catalysts, such as sodium hydroxide (NaOH), potassium hydroxide (KOH) or sodium carbonate ($Na_2CO_3$), are used to prepare low-molecular-weight polyethylene glycol.

According to another advantageous embodiment of the method of the invention, said stage of supplying PE, such as PEG and/or PPG, from respectively ethylene oxide (EO) and/or propylene oxide (PO), in the method of the invention further includes a prior stage of production of said ethylene oxide from ethylene and/or a prior stage of production of said propylene oxide from propylene; the ethylene and/or the propylene being derived from renewable raw materials.

The production of ethylene oxide from ethylene generally involves the direct oxidation of the ethylene by air or oxygen. A method of direct oxidation of ethylene by oxygen, in the presence of a catalyst between 240 and 270° C. and at a pressure of 15 to 25 atm (1.5 to 2.5 Mpa) is preferably used according to the reaction: $C_2H_4 + \frac{1}{2} O_2 \rightarrow C_2H_4O$ There are two principal methods for obtaining propylene oxide and propylene: the conventional ex-chlorohydrin route and catalytic epoxidation. In the conventional ex-chlorohydrin route, the propylene reacts with chlorine in an aqueous medium so as to give a chlorohydrin which is dehydrochlorinated in the presence of $Ca(OH)_2$. In catalytic epoxidation, three hydroperoxides have an industrial importance: that of the tert-butyl, that of ethylbenzene and propylene peroxide. By reacting with propylene, they produce propylene oxide.

According to yet another embodiment, said stage of supplying PE (PEG and/or PPG) from ethylene and/or propylene in the method of the invention further comprises a prior stage of production of said ethylene and/or of said propylene from renewable raw materials.

By way of example, the production of ethylene from renewable raw materials comprises the following stages:

a) fermentation of renewable raw materials and, optionally, purification in order to produce at least one alcohol selected from ethanol and the mixtures of alcohols comprising ethanol;

b) dehydration of the alcohol obtained in order to produce, in a first reactor, at least one alkene selected from ethylene and mixtures of alkenes comprising ethylene, and, optionally, purification of the alkene in order to obtain ethylene.

As renewable raw materials for the production of ethylene or propylene, use may be made of vegetable raw materials, materials of animal origin or materials of plant or animal origin which are derived from recovered materials (recycled materials). In the sense of the invention, the materials of vegetable origin contain at least sugars and/or starches. The vegetable materials containing sugars are essentially sugar cane and sugar beet; mention may also be made of maple, date palm, sugar palm, sorghum, American agave; the vegetable materials containing starches are essentially cereals and legumes such as corn, wheat, barley, sorghum, soft wheat, rice, potato, cassava, sweet potato, or else algae. Among the materials derived from recovered materials, mention may in particular be made of vegetable waste or organic waste comprising sugars and/or starches. Preferably, the renewable raw materials are vegetable materials.

As renewable raw materials, use may also be made of cellulose or hemicellulose, or even lignin, which, in the presence of the appropriate microorganisms, can be converted into materials comprising sugar. Among these renewable materials are straw, wood and paper, which can advantageously originate from recovered materials. Among the materials derived from recovered materials, mention may in particular be made of vegetable waste or organic waste comprising sugars and/or polysaccharides. The lists provided above are not limiting.

The fermentation of the renewable materials is carried out in the presence of one or more appropriate microorganisms; this microorganism may optionally have been naturally modified by a chemical or physical constraint, or genetically modified, and the term mutant is then used.

Conventionally, the microorganism used for the production of ethylene is *Saccharomyces cerevisiae* or a mutant thereof.

Preferably, the fermentation stage is followed by a purification stage intended to separate the ethanol from the other alcohols.

In stage b) the alcohol(s) obtained is (are) dehydrated in order to produce, in a first reactor, at least one alkene selected from ethylene and mixtures of alkenes comprising ethylene, the by-product of the dehydration being water.

Generally, the dehydration is carried out using an alpha-alumina-based catalyst, such as the catalyst sold by Euro-support under the trade name ESM 110® (undoped trilobed alumina containing little—approximately 0.04%—residual $Na_2O$).

The operating conditions for the dehydration are part of the general knowledge of those skilled in the art; by way of indication, the dehydration is generally carried out at a temperature of the order of 400° C.

Another advantage of the method according to the invention is its energy saving: the fermentation and dehydration stages of the method according to the invention are carried out at relatively low temperatures, less than 500° C., preferably less than 400° C. In comparison, the stage of cracking and steam cracking of oil to give ethylene is carried out at a temperature of the order of 800° C. This energy saving is also accompanied by a decrease in the amount of $CO_2$ released into the atmosphere.

Preferably, a purification stage is carried out during stage a) or during stage b). The optional purification stages (purification of alcohol(s) obtained in stage a), purification of alkene(s) obtained in stage b)) are advantageously carried out by absorption on conventional filters, such as molecular sieves, zeolites, carbon black, etc.). If the alcohol obtained in stage a) has been purified so as to isolate the ethanol, the alkene obtained in stage b) is ethylene. If the alcohol obtained in stage a) has not been purified, a mixture of alkenes comprising ethylene is obtained at the end of stage b).

Advantageously, at least one purification stage is carried out during stage a) and/or stage b) in order to obtain ethylene having a purity of greater than 85% by weight, preferably than 95% by weight, preferably than 99% by weight and most preferentially than 99.9% by weight. Particularly preferably, the alcohol obtained in stage a) is purified so as to isolate the ethanol; the alkene obtained in stage b) is consequently ethylene.

The principal impurities present in the ethylene derived from the dehydration of ethanol are ethanol, propane and acetaldehyde. Advantageously, the ethylene will have to be purified, i.e. the ethanol, the propane and the acetaldehyde will have to be eliminated, in order to be able to easily oxidize the ethylene. The ethylene, the ethanol, the propane and the acetaldehyde can be separated by carrying out one or more distillations at low temperature. The boiling points of these compounds are the following:

| Compound | Boiling point (° C.) |
| --- | --- |
| ethylene | −103.7 |
| propane | −42.1 |
| acetaldehyde | 20.8 |
| ethanol | 75.5 |

The ethylene, the ethanol, the propane and the acetaldehyde are cooled to approximately −105° C., preferably −103.7° C., and then distilled in order to extract the ethylene.

Another advantage of the method according to the present invention concerns the impurities. The impurities present in the ethylene derived from the dehydration of ethanol are completely different from those present in the ethylene derived from cracking or steam cracking. In particular, among the impurities present in the ethylene derived from cracking or steam cracking are dihydrogen and methane, regardless of the composition of the initial charge. Conventionally, the separation of the dihydrogen and the methane is carried out after compression at 36 bar and cooling to approximately −120° C. Under these conditions, the dihydrogen and the methane, which are liquid, are separated in the demethanizer; then the ethylene is recovered at 19 bar and −33° C. The method according to the present invention makes it possible to do away with the stage for separating the dihydrogen and the methane, and also makes it possible to cool the mixture to −105° C. at atmospheric pressure instead of −120° C. at 36 bar. The cooling in this separation stage can also be carried out under pressure in order to increase the boiling point of the compounds to be separated (for example around 20 bar and −35° C.) These differences also contribute to making the method according to the invention more economical (savings in terms of material and energy, which is also accompanied by a decrease in the amount of $CO_2$ released into the atmosphere).

Another advantage is that the ethylene obtained in stage b) of the method according to the invention does not comprise acetylene, unlike the ethylene obtained by cracking or steam cracking. As it happens, acetylene is very reactive and causes oligomerization side-reactions; the obtaining of ethylene without acetylene is therefore particularly advantageous.

Another advantage is that the method according to the invention can be carried out in production units located on the production site of the raw materials. In addition, the size of the production units in the method according to the invention is much smaller than the size of a refinery: refineries are in fact large plants which are generally located far from the raw material production centers and are supplied by means of pipelines.

By way of example, the production of propylene from renewable raw materials comprises the following stages:
  a') fermentation of renewable raw materials, and, optionally, purification, in order to produce an alcohol or a mixture of alcohols, said alcohol or mixture of alcohols comprising at least isopropanol and/or at least one mixture of ethanol and/or 1-butanol,
  b') dehydration of the alcohol or of the mixture of alcohols obtained for the purpose of producing, in at least one first reactor, an alkene or a mixture of alkenes, said alkene or mixture of alkenes comprising at least propylene, and, optionally, purification of the mixture of alkenes in order to obtain propylene.

These stages a) and b) are in particular described in application FR0858244.

As renewable raw materials, those already defined above are used. In the case of polysaccharides, the vegetable material used is generally in hydrolyzed form before the fermentation stage. This preliminary hydrolysis stage thus allows for, for example, saccharification of the starch in order to convert it to glucose, or conversion of the sucrose to glucose.

The fermentation of the renewable materials is carried out in the presence of one or more appropriate microorganisms; this microorganism may optionally have been naturally modified by a physical or chemical constraint, or genetically modified, and the term mutant is then used.

Advantageously, the microorganism used for the production of propylene is *Clostridium beijerinckii* or a mutant thereof, preferably immobilized on a support of the calcium or polymer fiber type. This fermentation makes it possible to obtain a mixture of alcohols comprising ethanol, isopropanol and 1-butanol. The alcohols obtained can be continuously extracted by means of a pervaporation membrane; an advantage of the use of this type of membrane is that of allowing better preservation of the microorganisms, since the latter are destroyed when their concentration becomes too high.

Other microorganisms that can be used are *Clostridium aurantibutyricum* or *Clostridium butylicum*, and also mutants thereof. The fermentation of these raw materials essentially results in the production of isopropanol and/or butanols with possibly acetone.

According to a first variant, the alcohol obtained is essentially isopropanol.

The fermentation stage is advantageously followed by a purification stage, for example a distillation intended to separate the isopropanol from the other alcohols.

According to this first variant, in stage b'), the isopropanol is dehydrated in order to produce, in a first reactor, at least propylene or a mixture of alkenes comprising propylene, the by-product of the dehydration being water.

Generally, the dehydration is carried out in the presence of oxygen and water using an alpha-alumina catalyst, such as the catalyst sold by Eurosupport under the trade name ESM 110® (undoped trilobed alumina containing little—approximately 0.04%—residual $Na_2O$).

The operating conditions for the dehydration are part of the general knowledge of those skilled in the art; by way of indication, the dehydration is generally carried out at a temperature of the order of 400° C.

An advantage of this method according to the invention is its energy saving: the fermentation and dehydration stages in the method according to the invention are carried out at relatively low temperatures, less than 500° C., preferably less than 400° C.; in comparison, the stage of cracking and steam cracking of oil to give propylene is carried out at a temperature of the order of 800° C.

This energy saving is also accompanied by a decrease in the amount of $CO_2$ released into the atmosphere.

According to a second variant, which can be implemented following a fermentation by means of *Clostridium beijerinckii* or a mutant thereof, a mixture of alcohols comprising at least ethanol and 1-butanol is obtained.

Advantageously, the fermentation stage is followed by a purification stage, for example a distillation intended to separate the ethanol and the 1-butanol from the other alcohols.

According to this second variant, stage b') is carried out by means of a series of reactors:

in a first part of the series of reactors (located at the inlet of the series of reactors in the direction of the passage of the fluids) the ethanol and the 1-butanol are dehydrated for the purpose of producing at least ethylene and 1-butene, this dehydration being carried out under the same conditions as the dehydration of isopropanol described above;

in a second part of this first series of reactors (located in the intermediate part of the series of reactors) a reaction in which 1-butene is hydroisomerized to give 2-butene is carried out;

in a third part of this first series of reactors (located at the outlet of the series of reactors in the direction of the passage of the fluids) metathesis of the ethylene and of the 2-butene is carried out in order to form propylene.

The details of the hydroisomerization and metathesis reactions are, for example, mentioned in patent application FR 2 880 018.

The reaction in which 1-butene is hydroisomerized to give 2-butene is generally carried out using a catalytic composition comprising a compound of a group VIII transition metal, and more particularly of palladium or of nickel. The catalytic composition may also comprise a quaternary ammonium and/or phosphonium salt, which makes it possible to carry out the reaction at a relatively low temperature, in a closed, semi-closed or continuous system.

The metathesis reaction is carried out by bringing the reactants into contact with a bed of catalyst; the metathesis is generally carried out continuously and comprises a reaction phase and a regeneration phase. The catalysts used contain rhenium oxide on alumina or an alumina-derived compound, for instance a silica-alumina or a boron oxide-alumina.

Preferably, the microorganism used is *Clostridium beijerinckii* or a mutant thereof; this microorganism can in fact be used to carry out the first variant and the second variant, thus the method can be carried out using isopropanol and/or the combination of ethanol and 1-butanol.

The optional purification stages (purification of alcohol(s) obtained in stage a'), purification of alkene(s) obtained in stage b')) are advantageously carried out by absorption on conventional filters, such as molecular sieves, zeolites, carbon black, etc.

Advantageously, at least one purification stage is carried out during stage a') and/or stage b') in order to obtain a propylene with a degree of purity sufficient to form a polymerization or a copolymerization. Propylene with a degree of purity of greater than 85% by weight, preferably than 95% by weight, preferably than 99% by weight and most preferentially than 99.9% by weight may preferably be obtained. The principal impurities present in the propylene derived from these dehydrations are acetone, diisopropyl ether, acetaldehyde, 1-propanol and hydrogen.

Advantageously, the propylene is purified, i.e. the acetone, the diisopropyl ether, the acetaldehyde, the 1-propanol and the hydrogen will have to be eliminated. The hydrogen, which has a boiling point much lower than that of propylene, can be isolated by compressing the gas and then cooling it slightly, for example at 19 bar and −33° C.

The propylene, the acetone, the diisopropyl ether, the acetaldehyde and the 1-propanol can be separated by carrying out one or more distillations at low temperature. The boiling points at atmospheric pressure of these compounds are the following:

| Compound | Boiling point (° C.) |
|---|---|
| propylene | −47.7 |
| acetaldehyde | 20.8 |
| acetone | 56 |
| diisopropyl ether | 68 |
| 1-propanol | 97 |

The propylene, the acetone, the diisopropyl ether, the acetaldehyde and the 1-propanol are cooled, at atmospheric pressure, to approximately −50° C., preferably −47.7° C., and then distilled in order to extract the propylene. This distillation can optionally be carried out under pressure in order to be able to extract the propylene at a higher temperature.

Another advantage of the method according to the present invention concerns the impurities. The impurities present in the propylene derived from the dehydration of the alcohols are completely different from those present in the propylene derived from cracking or steam cracking. In particular, among the impurities present in the propylene derived from cracking or steam cracking are methylacetylene and propadiene.

With the method according to the present invention, methylacetylene and propadiene are also obtained, but these compounds are then present in much lower amounts. This difference makes it possible to limit the risks linked to the very reactive nature of methylacetylene and also to limit the oligomerization side-reactions. Another advantage is that the method according to the invention can be carried out in production units located on the raw material production site. In addition, the size of the production units in the method according to the invention is much smaller than the size of a refinery: refineries are in fact large plants which are generally located far from the raw material production centers and are supplied by means of pipelines. All these differences contribute to making the method according to the invention more economical (saving in terms of material and energy, which is also accompanied by a decrease in the amount of $CO_2$ released into the atmosphere) than the conventional methods for obtaining propylene.

The copolymers comprising PEG blocks obtained according to the method of the invention have good properties in terms of density, uptake of water and/or mechanical properties, antistatic properties, breathable waterproof properties and leaktight properties. The copolymers comprising PPG blocks obtained according to the method of the invention have good properties, in terms of low uptake of moisture, and in terms of stability of the mechanical properties with respect to ambient moisture. The copolymers comprising both PEG and PPG blocks of the invention have a combination of these advantageous properties. The method of the invention makes it possible to readily modulate these properties by varying the PEG/PPG ratio.

Finally, the method according to the invention makes it possible to obtain a block copolymer from ethylene oxide and/or propylene oxide of renewable origin, and with performance that is identical (or even better) than that of the corresponding copolymers (same chemical formula) but of fossil origin. Finally, the method of manufacture of block copolymers of the invention makes it possible to reduce, or even completely eliminate the consumption of raw materials of petroleum origin, and use raw materials obtained from the growing of plants. Furthermore, it makes it possible to reduce emissions of greenhouse gases.

The invention claimed is:

1. A block copolymer consisting of:
   1) from 5 to 95% by mass based on the total mass of said copolymer of at least one polyether flexible block derived at least partially from polyethylene glycol or a mixture of polyethylene glycol and polypropylene glycol, containing $^{14}C$ determined in accordance with standard ASTM D6866, and said polyether flexible block has at least one polyethylene glycol which is derived at least partially from renewable materials and
   2) from 5 to 95% by mass based on the total mass of said copolymer, of at least one rigid block, said rigid block being derived at least partially from renewable raw materials, wherein the rigid block is comprised of polyamide blocks and at least one polyurethane block, wherein said copolymer comprises a content of biocarbon above 5%, which corresponds to a $^{14}C/^{12}C$ isotope ratio of at least $1.2 \times 10^{-14}$.

2. The copolymer as claimed in claim 1, wherein said at least one polyether flexible block and/or said at least one rigid block is/are derived totally from renewable materials.

3. The copolymer as claimed in claim 1, wherein the polyamide blocks of said rigid block contain at least one copolyamide.

4. The copolymer as claimed in claim 1, wherein said at least one polyether flexible block additionally contains polyethers other than polyethylene glycol.

5. The copolymer as claimed in claim 4, wherein said at least one polyether flexible block contains PO3G, PTMG or poly(3-methyltetrahydrofuran) of renewable origin or of fossil origin and/or polyethylene glycol or polypropylene glycol of fossil origin.

6. The copolymer of claim 1, wherein
   said at least one polyether flexible block is from 5 to 85% of the total mass of the copolymer, and
   said at least one rigid block is from 5 to 85% of the total mass of the copolymer.

7. The copolymer as claimed in claim 1, wherein said content of biocarbon is above 25%.

8. The copolymer as claimed in claim 7, wherein said content of biocarbon is above 75%.

9. The copolymer as claimed in claim 8, wherein said content of biocarbon is above 98%.

10. The copolymer of claim 1, wherein the polyether flexible block is derived at least partially from ethylene obtained from the renewable starting materials, wherein the ethylene has been subjected to purification, and wherein the purification comprises the removal of ethanol, propane and acetaldehyde, wherein the purification stage results in a degree of purity greater than 99%.

11. The copolymer of claim 10, wherein the purification comprises one or more low temperature distillations.

12. The copolymer of claim 10, wherein the purification comprises a distillation at a temperature of −103.7° C. or lower.

13. The copolymer of claim 12, wherein the distillation is at atmospheric pressure.

14. The copolymer of claim 10, wherein the purification stage results in a degree of purity greater than 99.9%.

15. The copolymer of claim 1, wherein the polyether flexible block is partially derived from propylene obtained from the renewable starting materials, wherein the propylene has been subjected to purification, and wherein the purification comprises the removal of ethanol, propane and acetaldehyde, wherein the purification stage results in a degree of purity greater than 99%.

16. The copolymer of claim 15, wherein the purification comprises one or more low temperature distillations.

17. The copolymer of claim 15, wherein the purification comprises a distillation at a temperature of −47.7° C. or lower.

18. The copolymer of claim 17, wherein the distillation is at atmospheric pressure.

19. The copolymer of claim 15, wherein the purification stage results in a degree of purity greater than 99.9%.

20. The block copolymer of claim 1, wherein the polyamide blocks of the rigid block contain one or more polyamide monomers selected from the group consisting of: 11, 5.4, 5.9, 5.10, 5.12, 5.13, 5.14, 5.16, 5.18, 5.36, 6.4, 6.9, 6.10, 6.12, 6.13, 6.14, 6.16, 6.18, 6.36, 10.4, 10.9, 10.10, 10.12, 10.13, 10.14, 10.16, 10.18, 10.36, 10.T, 12.4, 12.9, 12.10, 12.12, 12.13, 12.14, 12.16, 12.18, 12.36, 12.T and mixtures thereof.

21. The block copolymer of claim 1, wherein at least one polyamide block of the rigid block is formed from the condensation of an aromatic dicarboxylic acid and an aromatic diamine.

22. An automobile, textile, woven fabric, nonwoven fabric, clothing, shoe, sports article, leisure article, electronic, computer equipment, health equipment, industrial additive, packaging and/or household product comprising a block copolymer according to claim 1.

23. The product as claimed in claim 22, wherein the block copolymer is used alone or mixed, said block copolymer representing by mass from 5 to 100% of said product.

24. In instrument panels, airbags, soles of sports shoes, golf balls, tubes for medical use, catheters, angioplasty balloons, peristaltic bands, conveyor belts, breathable waterproof rainwear, antistatic additives, skin panels, and/or synthetic leather, thermoplastic films, packaging films comprising a block copolymer, the improvement wherein the block copolymer is a block copolymer according to claim 1.

25. A method for preparing the block copolymer as claimed in claim 1, comprising the stage of supplying polyether derived at least partially from ethylene oxide containing $^{14}C$ and conversion by synthesis to a block copolymer.

26. The method as claimed in claim 25, characterized in that said polyether comprises polyethylene glycol having a biocarbon content of at least 1%.

27. The method as claimed in claim 25, wherein the supply stage comprises a stage of production of polyether from ethylene oxide having a biocarbon content of at least 1%.

28. The method as claimed in claim 27, wherein the supply stage comprises a stage of production of said ethylene oxide from ethylene.

29. The method as claimed in claim 28, wherein the supply stage comprises a stage of production of said ethylene from plant biomass.

30. The method as claimed in claim 29, wherein the production of ethylene from renewable raw materials comprises the following stages:
  a) fermentation of renewable raw materials and, optionally, purification in order to produce at least one alcohol selected from ethanol and mixtures of alcohols comprising ethanol;
  b) dehydration of the alcohol obtained in order to produce, in a first reactor, at least one alkene selected from ethylene and mixtures of alkenes comprising ethylene, and, optionally, purification of the alkene in order to obtain ethylene.

* * * * *